(12) United States Patent
Yudkovitch et al.

(10) Patent No.: US 8,326,545 B2
(45) Date of Patent: *Dec. 4, 2012

(54) SYSTEM AND METHOD FOR DISPLAYING A PHARMACOKINETIC AND PHARMACODYNAMIC DRUG MODEL

(75) Inventors: Laurence M. Yudkovitch, Mequon, WI (US); Ronald P. Makin, Fitchburg, WI (US); Rene J. C. Coffeng, Helsinki (FI); Toni M. Taiminen, Vantaa (FI)

(73) Assignee: General Electric Company, Schenectady, NY (US)

( * ) Notice: Subject to any disclaimer, the term of this patent is extended or adjusted under 35 U.S.C. 154(b) by 1736 days.

This patent is subject to a terminal disclaimer.

(21) Appl. No.: 11/619,880

(22) Filed: Jan. 4, 2007

(65) Prior Publication Data

US 2008/0097167 A1    Apr. 24, 2008

Related U.S. Application Data

(60) Provisional application No. 60/829,963, filed on Oct. 18, 2006.

(51) Int. Cl.
*G06F 19/00* (2011.01)
*A61M 16/00* (2006.01)
*G06F 3/00* (2006.01)

(52) U.S. Cl. ............... 702/19; 128/203.12; 128/203.13; 128/203.25; 128/204.18; 128/204.21; 128/204.26; 128/205.23

(58) Field of Classification Search .................. None
See application file for complete search history.

(56) References Cited

U.S. PATENT DOCUMENTS

| | | | |
|---|---|---|---|
| 6,937,257 B1 | 8/2005 | Dunlavey | |
| 7,693,697 B2 | 4/2010 | Westenskow et al. | |
| 2003/0145854 A1* | 8/2003 | Hickle | 128/204.18 |
| 2003/0156143 A1 | 8/2003 | Westenskow | |
| 2006/0081244 A1 | 4/2006 | Bouillon et al. | |
| 2008/0033661 A1 | 2/2008 | Syroid et al. | |
| 2008/0091084 A1* | 4/2008 | Yudkovitch et al. | 600/300 |
| 2008/0108970 A1 | 5/2008 | Viertio-Oja | |

FOREIGN PATENT DOCUMENTS

WO    WO 02/32036    4/2002

OTHER PUBLICATIONS

Eger Anesth. Analg. (2001) vol. 93, pp. 947-953.*
Hendrickx et al. Anesth. Analg. (1997) vol. 84; pp. 413-418.*
Nickalls et al. Brit. J. Anesth. (2003) vol. 91; pp. 170-174.*
Rosenbaum et al. Anesth. Analg. (2003) vol. 97; pp. 1414-1420.*
Woehlck et al. J. Clin. Monit. Comput. (2000) vol. 16; pp. 535-540.*
Minto, C.F. et al. Response Surface Model for Anesthetic Drug Interactions. Anesthesiology 92, (2000), pp. 1603-1616.
Parker, R.S. et al. Control-relevant modeling in drug delivery. Advanced Drug Delivery Reviews 48, (2001), pp. 211-228.
Short, T.G. et al. Hypnotic and anaesthetic interactions between midazolam, propofol and alfentanil. British Journal of Anaesthesia 69, (1992), pp. 162-167.
Vuyk, J. Pharmacokinetic and Pharmacodynamic Interactions Between Opioids and Propofol. Journal of Clinical Anesthesia 9, (1997), pp. 23S-26S.
Office Action dated Jan. 19, 2011.
Office Action dated Mar. 1, 2011.
Office Action dated Apr. 19, 2011, for U.S. Appl. No. 11/564,005.
Drews et al., "Drug Delivery as Control Task: Improving Performance in a Common Anesthetic Task", Human Factors: The Journal of the Human Factors and Ergonomics Society, Spring 2006, 48(1):85-94.
Gurushanthaiah et al., "Visual Display Format Affects the Ability of Anesthesiologists to Detect Acute Physiologic Changes: A Laboratory Study Employing a Clinical display Simulator", Anesthesiology, Dec. 1995, 83 (6):1184-1193.
Kennedy et al., The effect of a model-based predictive display on the control of end-tidal sevoflurane concentrations during low-flow anesthesia, Anesthesia & Analgesia, Oct. 2004, 99(4):1159-1163.
Syroid et al., "Development and evaluation of a graphical anesthesia drug display", Anesthesiology, Mar. 2002, 96(3):565-575.
McGuire (Example User Interfaces for Various Caregivers; Copyright 2000, http://www.uprforum.com/Chap12.htm, p. 1-59).
Office Action dated Aug. 17, 2010.

* cited by examiner

*Primary Examiner* — Lori A Clow
(74) *Attorney, Agent, or Firm* — Andrus, Sceales, Starke & Sawall, LLP (57) ABSTRACT

A system and method for displaying a pharmacokinetics/pharmacodynamics drug model for a patient is provided. A monitor is arranged to detect a quantity of anesthetic agent provided to a patient by an anesthesia machine. A display is provided for displaying real-time pharmacokinetics data associated with the quantity of anesthetic agent provided to the patient. Safety control means are provided to initiate the display of real-time pharmacokinetics data for the anesthetic agent only when a predetermined threshold value for the anesthetic agent is detected by the monitor. Alternately, control means are adapted to terminate display of real-time pharmacokinetics data for the anesthetic agent when a predetermined threshold value for the anesthetic agent is detected by the monitor.

18 Claims, 5 Drawing Sheets

SYSTEM AND METHOD FOR DISPLAYING A PHARMACOKINETIC AND PHARMACODYNAMIC DRUG MODEL

CROSS REFERENCE TO RELATED APPLICATIONS

This application claims priority under 35 U.S.C. §119(e) of the co-pending U.S. Provisional Application No. 60/829,963, filed on Oct. 18, 2006 and entitled "SYSTEM AND METHOD FOR DISPLAYING A PHARMACOKINETIC AND PHARMACODYNAMIC DRUG MODEL."

BACKGROUND OF THE APPLICATION

In the operating room, the anesthesiologist needs to assess the patient's condition and adjust the therapy using a wide variety of distinct medical devices. These devices often don't talk to each other, and hence only provide one piece of the picture. Clinicians have to mentally keep track of the patient's level of sedation, analgesia and relaxation based on the amount of drugs they've administered, and their familiarity with the drug's pharmacokinetic and pharmacodynamic (PK/PD) models.

The practice of intra-operative anesthesia typically involves administering sedative, analgesic and neuromuscular relaxants to a patient. These drugs manage the patient's level of consciousness, pain management and neuromuscular blockade. Typically, each drug has a PK/PD model that specifies what the body does to the drug (pk) and how the drug interacts with the body (pd). These models are usually derived in isolation. In a clinical setting, multiple drugs are typically used together.

Three-dimensional response surfaces have been developed to represent the interaction between two drugs. These surfaces represent the probability of non-response to a specific effect at different concentrations of the two drugs. This can also be considered an interactive (or synergistic) pd model. The challenge is to display these varying probabilities on a 2d graph that can be easily interpreted by a clinician during anesthesia.

The issue is confounded even more when there is more than one effect to display on the same graph. For example, when considering analgesia, one can consider varying levels of pain such as high pain (intubation) and low pain (post-operative anesthesia). The challenge is to display these related but distinct surfaces on the same two-dimensional graph. The display should consist of the (effect site) concentration of the analgesic drug(s) (which is at least one input to the 3d surface), the probability of each displayed effect, and reference points to those effects (such as 50% to 95% probability).

Prior work by Medvis & the University of Utah developed a display to show PK/PD models to the clinician in real time. This work did not factor in some of the safety issues needed to safely use the system in a clinical environment. For example, it showed the models for inhaled agents as soon as the patient monitor detected them. The problem with this approach is that small traces of agents may be left over in the breathing circuit, although they are not largely part of the anesthesia plan for the patient.

Another issue not addressed in the prior art is how to handle communication errors with the connected devices. The display is fully reliant on getting accurate and timely information from the connected devices, specifically the anesthesia machine, patient monitor and/or IV pumps. If communication is severed, there is no clear path for what the display should show.

Another concern with known systems is that clinicians can continue old cases, instead of starting new ones. This is problematic since the previous patient's drug levels might be included with the next patient's levels, and that would lead to inaccurate predictions.

SUMMARY OF THE APPLICATION

The present invention resolves many drawbacks found in the above-described prior art systems. In the illustrated example, a system for displaying a PK/PD drug model for a patient is provided. The system includes a treatment device, such as an anesthesia machine for providing an anesthetic agent to a patient. A monitor is included that detects a quantity of anesthetic agent provided to the patient. The system also includes a display for displaying real-time PK/PD data associated with the anesthetic agent provided to the patient. Safety control means are adapted to initiate the display of real-time PK/PD data for the anesthetic agent only when a predetermined threshold value is detected by the monitor. Advantageously, small traces of anesthetic agents that are left over in a patient breathing circuit can be selectively disregarded when considering the anesthesia plan for the patient. In another example, the safety control means are adapted to initiate or terminate display of real-time PD models when a predetermined interaction threshold value for the anesthetic agent is detected by the monitor.

Advantageously, when accurate and timely information is not provided by the connected devices, such as the anesthesia machine, patient monitor and/or pumps, the control means is further adapted to clear the display of real-time PK/PD data and/or display an error message. In another example, the control means suggests starting a new case and clearing all information when it detects a low likelihood of an ongoing case. The system therefore decreases the likelihood that clinicians would mistakenly continue old cases, instead of starting new ones.

A method is also provided for displaying a real-time PD/PK drug model for a patient. In the illustrated embodiment, the method can include the steps of (1) detecting a quantity of the anesthetic agent provided to the patient and (2) displaying real-time PK/PD data associated with the quantity of the anesthetic agent only when a predetermined threshold value for the anesthetic agent is detected by the monitor.

BRIEF DESCRIPTION OF THE DRAWINGS

The drawings illustrate preferred embodiments and the best mode presently contemplated of carrying out the invention. In the drawings.

DETAILED DESCRIPTION OF THE DRAWINGS

Figure 1:
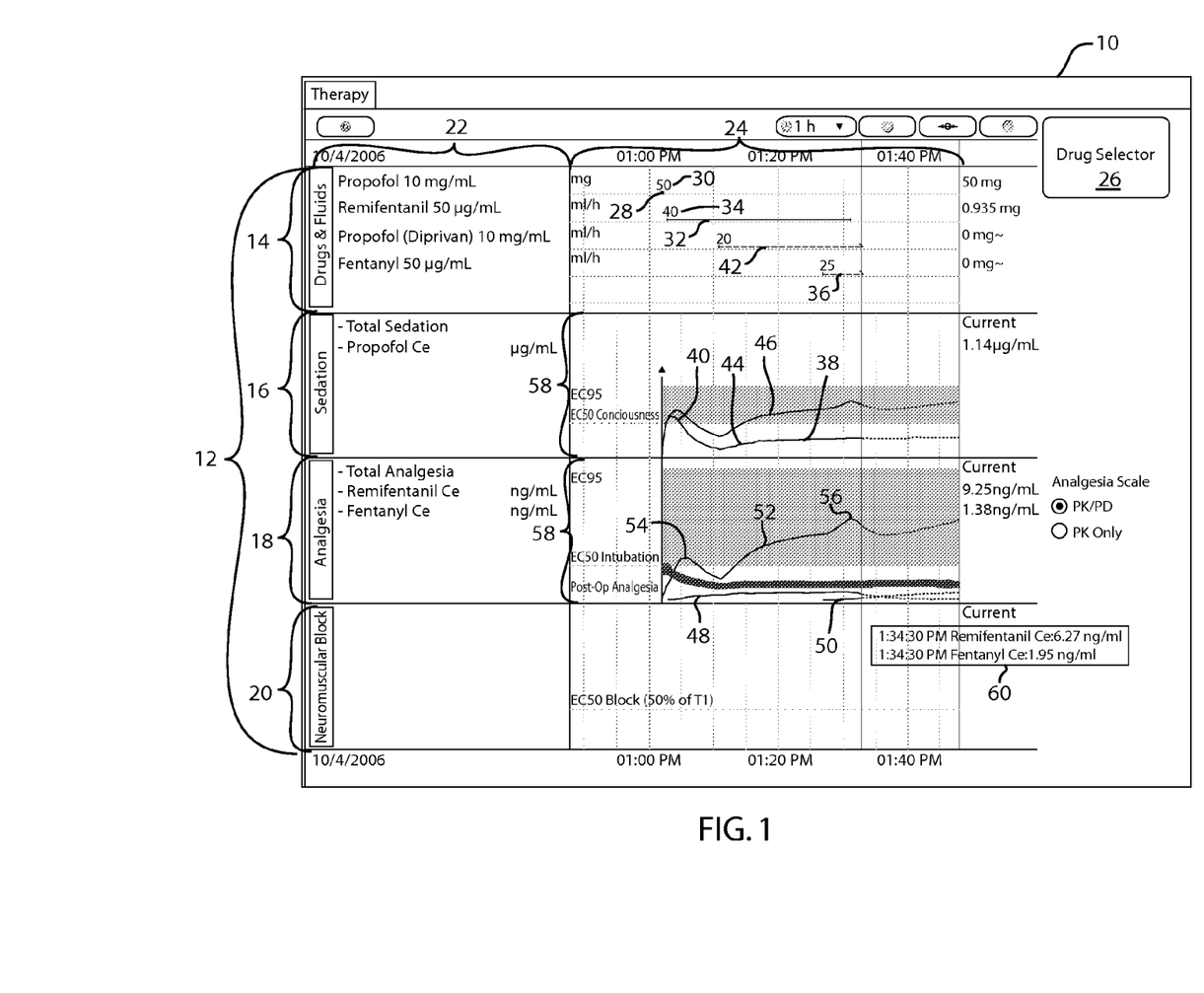
FIG. 1 is a screenshot of an embodiment of the user interface.

FIG. 1 depicts an embodiment of a user interface 10 for displaying drug administration documentation data and graphs based on the pharmacokinetic (PK) models and the pharmacodynamic (PD) models of the administered drugs.

The user interface 10 may be displayed by any display or display associated with a device that may be present in a close proximity to a clinician providing anesthetic agents to a patient. Such a display may be a terminal for a computer workstation and may comprise CRT or flat-screen technology. Furthermore, the display may be such that the clinician interacts with the user interface 10 using touch-screen technology that is activated by the clinician's finger or a stylus, or alternatively the clinician controls a cursor with a mouse, data knob, or a directional pad. The user interface 10 comprises a plurality of windows 12. Embodiments of the user interface 10 may include a drug administration window 14, a sedation window 16, an analgesia window 18, and a neuromuscular block window 20. Each of the windows may comprise two regions, a drug listing region 22 and a time-based graph region 24.

A clinician may enter drug administration data by selecting a drug selector button 26. Alternatively, the clinician may enter drug administration data by selecting the drug administration window 14. The drug selector button 26 may open a drug library (not depicted) that can be edited by the hospital to include the potential anesthetic drugs that could be administered to a patient. Also, the drug library may include the drug concentrations that are available. Many anesthetic drugs have been studied to develop pharmacokinetic and pharmacodynamic models for the drugs based on basic patient demographic information such as age, sex, height, and weight. The drug library may include an indication of which drugs in the library have associated PK and PD models. Anesthesia can be divided into three basic effects: sedation (patient consciousness), analgesia (patient pain blocking), and neuromuscular blocking patient relaxation). Each of the drugs in the drug library has a defined primary anesthetic effect. However, it is understood that any of the drugs may have effects in the other areas of anesthetic effect besides the drug's primary effect.

Once a clinician has selected a drug administration to document, the clinician may be prompted to enter the amount of the drug that was administered and the time at which the drug was administered. Further, the clinician may indicate that the administration was in the form of an injected bolus or as an IV infusion. Alternatively, if the device that is displaying the user interface 10 is connected to an IV infusion pump and the devices are able to properly communicate with each other the user interface may obtain drug infusion data such as the infusion rate and the infusion start and stop times from the infusion pump.

The user interface 10 displays the drug administration data in the drug administration window 14. The name of the drug appears in a listing in the drug listing region 22 of the drug administration window 14. As the administration of additional drugs are documented, these drugs are added to the bottom of the list. In an embodiment of the user interface 10, if more drugs have been administered than there is room for the drug administration window 14 to display, a scroll bar (not depicted) may appear, allowing a clinician to scroll through all of the documented drug administrations.

Additional drug administration data associated to the drugs listed in the drug listing region 22 is displayed in the graph region 24 of the drug administration window 14. For example, the drug Propofol is listed in the drug listing region 22. The number next to the name Propofol, "10 mg/ml" identifies the concentration of Propofol delivered. In the graph region 24 a dot 28 indicates a bolus of Propofol was delivered at approximately 1:02 PM. A drug amount indicator 30 identifies that 50 mg of Propofol was delivered in the bolus. Alternatively, the drug Remifentanil is listed in the drug listing region 22 at a concentration of 50 ug/ml In the graph region 24, a line 32 indicates that an infusion of Remifentanil was delivered at approximately 1:03 PM. A drug rate indicator 34 identifies that the infusion was at a rate of 40 ml/hour. The line 32 is a solid line, thus indicating that the infusion has been completed, in this case the infusion represented by line 32 ended at approximately 1:31 PM. A dotted line, such as line 36 indicates that an infusion is presently ongoing, as the infusion of the drug Fentanyl indicated by line 36.

An embodiment of the user interface 10 allows for the documentation of a drug administration retroactively. This means that the clinician is allowed to enter the time of a drug administration when documenting a drug administration rather than the drug administration being only recorded in real time when the clinician documents it. Furthermore, once a drug administration has been documented by the clinician, the clinician can edit the drug administration data to correct any mistakes in the documentation, or to update the information, such as recording when an infusion of a drug ends.

The user interface 10 displays the proper pharmacokinetic (PK) models and pharmacodynamic (PD) models for each of the drugs documented by the clinician appearing in the drug administration window 14. The pharmacokinetic models and the pharmacodynamic models are displayed on a graph separately from the drug administration window 14. In an embodiment of the user interface 10, the user interface 10 further comprises the sedation window 16, the analgesia window 18, and the neuro muscular block window 20. As previously stated, each drug is classified as to the primary anesthetic effect of the drug. This primary anesthetic effect determines which window the PK and PD models for each drug are depicted.

The sedation window 16 displays the PK graph based on the PK model for any drugs that have a primary anesthetic effect as a sedative. Propofol has a primary effect as a sedative; therefore, Propofol is listed in the drug listing region 22 of the sedation window 16. The Propofol PK graph 38, displaying the effect site concentration of Propofol, is then displayed in the graph region 24 of the sedation window 16. The Propofol PK graph 38 is affected by the amount of Propofol administered, the time the Propofol was administered, and the characteristics of the Propofol PK model. Therefore, an initial spike 40 in the Propofol effect site concentration appears shortly after the administration of the 50 mg bolus 28, followed by decay until the initiation of the 20 ml/hr infusion of Propofol 42, which produces an increase 44 in the effect site concentration of Propofol.

The sedation window 16 also displays a sedation PD graph 46 based on a sedation PD model for any drugs that have an anesthetic effect as a sedative. The sedation PD graph 46 may include data from drugs that have also been delivered to the patient that are not a sedative in primary effect, but may still produce some sedative effect. As a result the sedation PD graph 46 is an indication of the total sedation of the patient.

The analgesia window 18 also displays the PK graphs based on the PK models for any drugs that have a primary anesthetic effect as an analgesic. In FIG. 1, both Remifentanil and Fentanyl have a primary effect as an analgesic, therefore the analgesia window 18 displays more than one PK graph simultaneously. Both a Remifentanil PK graph 48 and a Fentanyl PK graph 50 appear in the graph region 24 of the analgesia window 18.

The analgesia window 18 also displays an analgesia PD graph 52 based on an analgesia PD model for any drugs that have any anesthetic effect as an analgesic. Therefore, despite Propofol having a primary effect as a sedative, Propofol also produces or contributes to an analgesic effect, and as such, a spike 54 in the analgesia PD graph 52 appears coinciding with the initial introduction of the 50 mg bolus 28 of Propofol. Furthermore, the analgesia PD graph 52 represents the combined analgesic effect of all of the administered drugs, therefore another spike 56 appears when the infusion of Fentanyl 36 is administered to the patient.

The graph region 24 of both the sedation window 14 and the analgesia window 16 comprise a normalized scale 58. The normalized scale 58 represents the percentage of the population that experiences a sedation or analgesic effect at a particular sedation or analgesia level. The normalized scale 58 then marks the level at which 50% (EC50) and 95% (EC 95) of the population experience the sedation or analgesic effect. The normalized scales 58 for sedation and analgesia PD graphs are specific to the sedation and analgesia PD models respectively. Additionally, the PK graphs are normalized to the normalized scale 58 also. The PK graphs are normalized to the effect site concentration required for an administration of that drug only to achieve the same sedation or analgesia effect.

While FIG. 1 does not display any information in the neurological block window 20, a similar display of neuromuscular PK and PD graphs, as described for the sedation window 14 and the analgesia window 16 is contemplated and considered to be within the scope of the present invention.

An embodiment of the user interface 10 further comprises a detailed information pop-up 60. A clinician using the user interface 10 in association with a device or display comprising an input means such as touch-screen technology or a cursor that is controlled by a input means such as a mouse, data knob, directional pad, or a keyboard can activate the detailed information pop-up 60 by touching or placing the cursor over any portion of a PK graph. The detailed information pop-up 60 appears on the user interface 10 and comprises detailed information regarding one or more PK graphs. The detailed information pop-up may identify a drug and present timing data and effect site concentration data for that drug at that point in time. Alternatively, another detailed information pop-up (not depicted) may similarly operate to provide detailed information regarding the PD graphs or drug administration data in the drug administration window.

The detailed information pop-up 60 improves the user interface 10 by keeping the windows 12 simple and easy to interpret, but allowing the clinician to have access to more detailed information regarding a particular portion of a PK or PD graph or a drug administration. The detailed information pop-up 60 also provides a solution to the tendency of the normalized scale 58 to suppress the PK graph in relation to the scale. The clinician can use the detailed information pop-up 60 to receive a more precise reading of effect site concentration than received by visual inspection of the PK graph.

Figure 2:
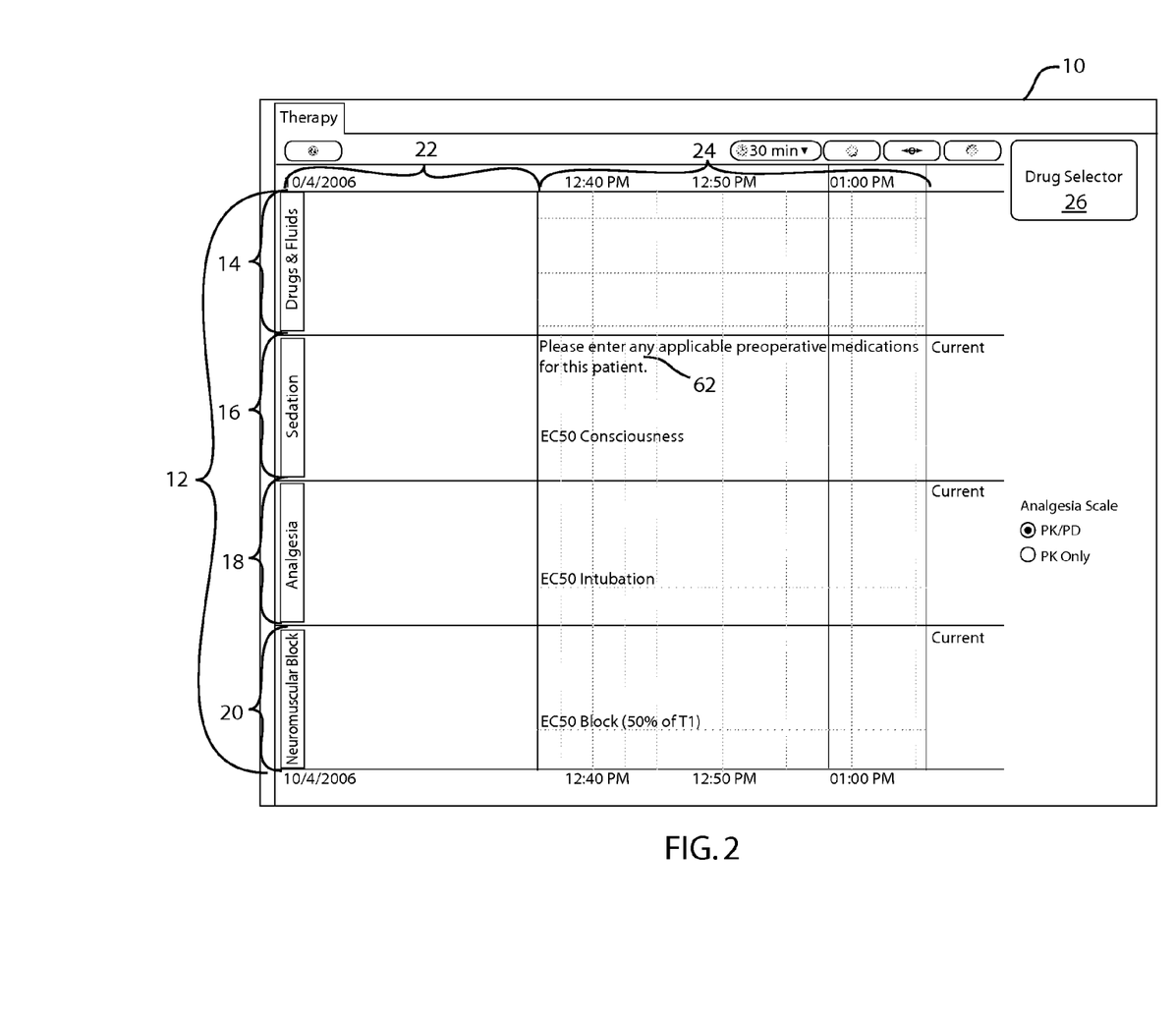
FIG. 2 is a screenshot of an embodiment of the user interface.

FIG. 2 depicts an embodiment of the user interface 10 as it may appear upon initialization of a program operating the user interface 10, before a clinician has documented the administration of any anesthetic drugs. The user interface 10 displays a pre-op warning message 62 located in the sedation window 16 that reminds the clinician to first enter into the user interface 10 any applicable preoperative medications that have already been administered to the patient. Alternatively, the pre-op warning message 62 may take the form of a text box or a textual message located in any of the other windows 12 of the user interface 10. This is an important safety feature because the clinician may forget to enter the preoperative medications that have been administered to the patient because the administration has already occurred. However, the presence of preoperative medications in the patient's body may have important effects on the PK or PD graphs for the drugs administered during the procedure.

Embodiments of the user interface 10 enhance the ease of use and understandability of the drug administration data and PK and PD graphs displayed on the user interface 10. A separated drug administration window 14 from the other windows displaying PK and PD graphs allows for the clinician to more easily track the documentation of drug administrations and provides the clinician with a clear record of what drugs were administered, when drugs were administered, how much drug was administered, and how the drug was administered.

Furthermore, the documentation of drug administration and the quality of the PK and PD models are improved in embodiments of the user interface 10. In embodiments of the user interface 10, the clinician is able to document the administration of drugs retroactively. This eliminates the need for an additional clinician to be present to perform the task of documenting the administration of drugs in real time, as required by user interfaces in the prior art. This has the added effect of helping to reduce the crowding that may be experienced in an operating room by reducing the number of people in the room by one. Additionally, if the clinician notices an error in the documentation of the administration of a drug, the clinician can edit the drug administration data to correct the error. The error correction ability improves the quality of the PK and PD graphs that are displayed as the PK and PD graphs are dependent upon the drug administration data.

Figure 3:
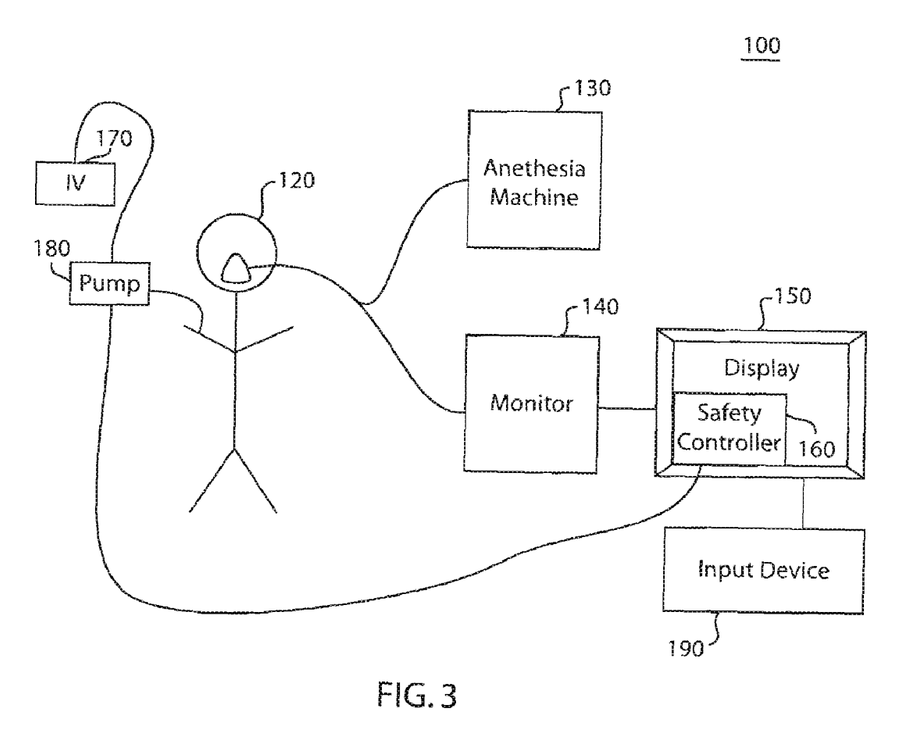
FIG. 3 illustrates a display system according to an embodiment of the present disclosure.

FIG. 3 illustrates a system 100 according to an embodiment of the present disclosure. The aforementioned user interface is implemented in the display 150 of the system 100. A patient 120 receives treatment from a treatment device or anesthesia machine 130 while being monitored by a patient monitor 140. The anesthesia machine 130 may include any device known or unknown capable of administering an anesthetic agent to the patient 120. Such anesthetic agent administered by the treatment device 130 may be in gaseous form and inhaled by the patient 120. An IV 170 and IV pump 180 are also provided and together provide anesthetic agents intravenously to the patient 120.

Still referring to FIG. 3, the monitor 140 is any monitor known in the art that is configured to detect the quantities of any anesthetic agents administered to the patient with the treatment device 130. The monitor 140 sends the measured quantities of anesthetic agents to a safety controller 160 implemented to control the user interface on the display 150 based upon the levels of anesthetic agent received from the monitor 140. In FIG. 3, the safety controller 160 is shown between the monitor 140 and display 150. However, it should be known that in other embodiments, the safety controller 160 may be implemented as part of the monitor 140, or part of the display 150. The safety controller 160 is configured to receive the quantity levels of the anesthetic agent in the patient 120, and to adjust the user interface on the display 150 to one of any of the following displays: basic display; an interactive display; or a display inhibited.

Figure 4:
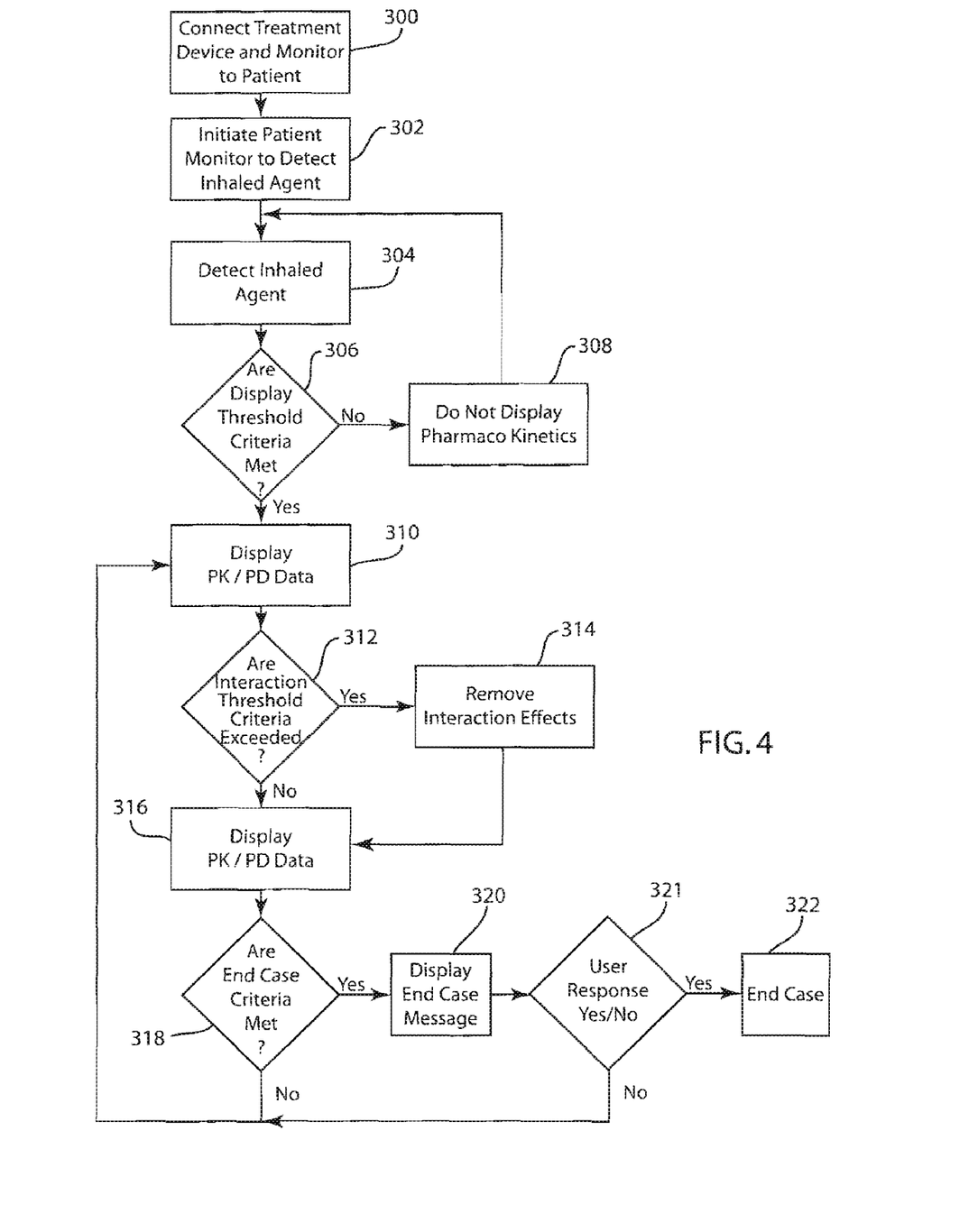
FIG. 4 is a flow chart illustrating a method for displaying a PK/PD drug model for a patient.

As shown in FIG. 4, a treatment device such as the anesthesia machine and a patient monitor are connected to the patient at step 300. At this step, the anesthesia machine is arranged to provide gaseous anesthetic agent to the patient via a patient circuit as is well known in the art. At step 302, the patient monitor is initiated to detect inhaled anesthetic agent provided to the patient. Once a positive value for inhaled anesthetic agent is detected at step 304, the safety control means inquires as to whether a predetermined set of threshold criteria are met at step 306. In a preferred embodiment, PK/PD values for inhaled anesthetic agents are calculated and shown when the fraction expired anesthetic agent (FeAA) is greater than a threshold of 0.3 percent and the fraction inspired anesthetic agent (FiAA) is not equal to the FeAA. Thereafter, the display of pharmacokinetics for inhaled agents is continued even if the FeAA becomes less than or equal to 0.3 percent. In the preferred embodiment, an exception applies for $N_2O$, wherein the PK/PD data is calculated and shown when the fraction expired (Fe) $N_2O$ is greater than about 3 percent and the fraction inspired (Fi) $N_2O$ is not equal to Fe $N_2O$. For $N_2O$, the PK/PD display is continued even if the value of Fe $N_2O$ becomes less than or equal to about 3 percent.

If the threshold value is not detected, the display of PK/PD data is not provided, as illustrated at step 308. If, however, the threshold criteria are met, the PK/PD data is displayed at step 310. It has been found that the above threshold values advantageously prevent initiation of PK/PD modeling in situations where the monitor detects trace amounts of anesthetic agent remaining in the patient circuit. The system thereby improves the accuracy of the PK/PD modeling process and eliminates opportunities for error.

Once the display is provided at 310, the safety control means are adapted to inquire whether interaction threshold criteria are met, at step 312. When considering the display of interaction models, there is a different threshold for when the inhaled agents may have an effect on the interaction models. Depending on the relationship of the anesthetic agent to the particular interaction model, this may permit the display of the model, or require its removal. The method and system of this embodiment of present invention therefore advantageously facilitate display or removal of such agents from the PK/PD modeling process. The preferred embodiment of the threshold criteria, described in the case where the anesthetic agent invalidates the model is as follows:

For Isoflurane, Sevoflurane, Enflurane or Halothane:
Interactions are labeled "unknown" ((FiAA>0.3%) OR (CeAA>0.3%) OR (EtAA>0.3%)); wherein CeAA is the (pharmacokinetic) effect site concentration at the site of effect (i.e. the patient's brain) for the particular anesthetic agent used. Effect site concentration is a time delayed version of the plasma concentration that accounts for the temporal delay between the blood concentration increasing, and the drug actually affecting the patient. The designation "EtAA" is the end tidal anesthetic agent value detected by the monitor.

For Desflurane:
Interactions are labeled "unknown" when ((FiAA>0.3%) OR (CeAA>0.3*($MAC_{age}$)) OR (EtAA>0.3%)); wherein $MAC_{age}$ is a variation on minimum alveolar concentration that accounts for patient age. Formulas for calculation of $MAC_{age}$ are known in the art.

For $N_2O$:
Interactions are labeled "unknown" when ((FiAA>0.3%) OR (CeAA>minCeAA) OR (EtAA>0.3%)); wherein minCeAA is a nomenclature to denote the minimum CeAA.

An alternate embodiment of this system, using fewer parameters, is implemented as follows:

For Isoflurane, Sevoflurane, Desflurane, Enflurane or Halothane:
Interactions are labeled "unknown" when (CeAA>0.3%*AgeMACawake); wherein AGEMACawake is a variation on MAC that accounts for age and adjusts to consciousness.

For $N_2O$:
Interactions are labeled "unknown" when (CeN$_2$O>0.1*AgeMACawake).

Note that specific threshold values provided above can vary based on the specific drug or system.

The above threshold values and results are expressed in the following table:

|  | MAC | Age MAC Awake | | | Interactions not shown over | | |
|---|---|---|---|---|---|---|---|
|  |  | 18 | 40 | 90 | 18 | 40 | 90 |
| Nitrous Oxide | 100 | 64.148 | 55.021 | 38.817 | 6.415 | 5.502 | 3.882 |
| Isoflurane | 1.15 | 0.459 | 0.394 | 0.278 | 0.138 | 0.118 | 0.083 |
| Sevoflurane | 2.05 | 0.819 | 0.702 | 0.495 | 0.246 | 0.211 | 0.149 |
| Desflurane | 6 | 2.396 | 2.055 | 1.450 | 0.719 | 0.617 | 0.435 |
| Enflurane | 1.7 | 0.679 | 0.582 | 0.411 | 0.204 | 0.175 | 0.123 |
| Halothane | 0.75 | 0.481 | 0.413 | 0.291 | 0.144 | 0.124 | 0.087 |

If the interaction threshold criteria are detected, the safety control means controls the display to remove the interaction effects at step 314. However, if the threshold criteria are not detected, the safety control means continues to display the PK/PD data on the display at step 316.

The safety control means is advantageously adapted to terminate the display of real-time PK/PD data if an "end case" criterion is met, at step 318. The system can advantageously use one or more of the following conditions (alone, or in combination) to detect when the case may be over, and automatically prompt the user to end the case:

Effect site concentration (Ce) for each drug stays below its respective EC05 for 15 mins; wherein EC05 is the effect site concentration at which 5% of the population will experience the effect.

Effect site concentration (Ce) for each analgesic drug stays below its EC01 for 15 mins; wherein EC01 is the effect site concentration at which 1% of the population will experience the effect.

One or more inhaled agents have a positive FIAA or ETAA, but all are below the display threshold for 15 mins.

Respiration rate (RR) and heart rate are invalid (i.e. !>0) or the monitor is disconnected (no patient case in progress).

The above conditions are also used to detect when the patient has been taken off the table.

If one of the above criteria are met, the system is adapted to display a prompt on display, such as: End case? [Yes|No]. Pressing 'yes' is equivalent to pressing the end case button. Pressing 'no' results in no change to the current case, and resets the counter to zero so that in 15 minutes, the system prompts the user again if the conditions remain valid.

If the above-described end case criteria are met, an end case prompt message is displayed at step 320, alerting the user to the fact that the case has been ended. At step 321, the system inquires as to the user response to the end case prompt is "no" or "yes". If it is "no", the PK/PD display is continued. If "yes", the case is ended at step 322. If the end case criteria are not met, the PK/PD display is continued, as shown at step 310.

Figure 5:
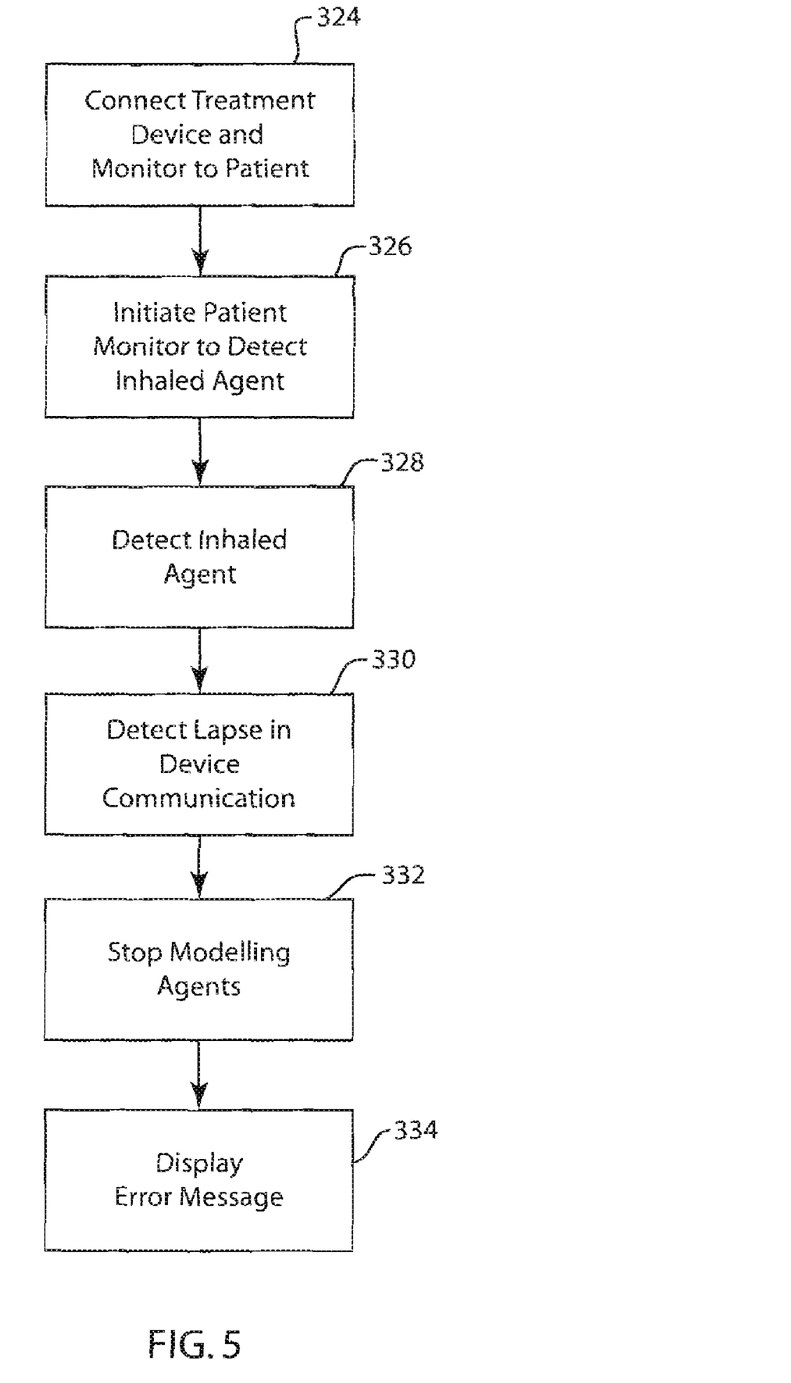
FIG. 5 is a flow chart illustrating another method for displaying a PK/PD drug model for a patient.

Referring to FIG. 5, when device connections fail, it's important to highlight that information to the user. When a device connection fails, the system displays an error message, and assumes the last rate continues. If the device is reconnected, the system probes the device for the missing information, and automatically fills it in. If there are gaps in the data, then users must manually correct it. For devices where the system does not support a manual correction (e.g. monitor communication), then the system cannot model those drugs in the future, and any restrictions on the system by not knowing those drugs must be imposed.

As a specific example, if the monitor connection is lost, the system displays a message "Monitor connection was lost—inhaled agents unknown" on the sedation graph. Modeling for any inhaled agents that had been detected previously must be stopped. The display of interaction effects must also be stopped, and cannot be resumed for the rest of the case. Even if the monitor connection is restored, modeling for inhaled agents is still restricted because the system does not know what transpired when it was down.

According to the illustrated embodiment, the treatment device and monitor are connected to the patient at step 324. The patient monitor is initiated to detect inhaled anesthetic agent provided to the patient at step 326. When the inhaled agent is detected at step 328, the system is arranged to detect a lapse in device communication at step 330. If the lapse in device communication is detected, the modeling of anesthetic agents is stopped at step 332 and an error message is displayed at step 334.

The present invention has been described in terms of specific embodiments incorporating details to facilitate the understanding of the principals of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A system for displaying a pharmacokinectic/pharmacodynamic (PK/PD) drug model for a patient, the system comprising:
   a treatment device, wherein the treatment device provides an anesthetic agent to the patient;
   a monitor, wherein the monitor detects a quantity of the anesthetic agent provided to the patient;
   a display, wherein real-time PK/PD data associated with the anesthetic agent is displayed on the display; and
   a safety controller, wherein the safety controller detects a predetermined fraction of anesthetic agent that exceeds a predetermined threshold value and further sends a signal to the display to initiates the display of real-time PK/PD data for the anesthetic agent, wherein the threshold value is equal to the value at which the agent has an effect on the PK/PD drug model, and further wherein the safety controller determines whether an interaction threshold is met, and removes any interaction effects.

2. The system of claim 1, wherein the monitor is arranged to detect the fraction of anesthetic agent expired by the patient and the fraction of anesthetic agent inspired by the patient, and wherein the safety controller only initiates the display of PK/PD data for the anesthetic agent when the fraction of expired anesthetic agent is greater than about 0.3% and when the fraction of expired anesthetic agent is not equal to the fraction of inspired anesthetic agent.

3. The system of claim 2, wherein the system continues to display pharmacokinetics data when the fraction of expired anesthetic agent becomes less than about 0.3%.

4. The system of claim 1, wherein the monitor is arranged to detect the fraction of anesthetic agent expired by the patient and the fraction of anesthetic agent inspired by the patient, wherein the anesthetic agent is $N_2O$, and wherein the safety controller only initiates display of PK/PD data for the $N_2O$ when the fraction of expired $N_2O$ is greater than about 3% and the fraction of expired $N_2O$ is not equal to the fraction of inspired $N_2O$.

5. The system of claim 4, wherein the system continues to display PK/PD data for the $N_2O$ when the fraction of expired $N_2O$ becomes less than about 3%.

6. The system of claim 1, wherein the safety controller is adapted to provide an error message on the display if the threshold value is detected.

7. The system of claim 6, wherein the error message indicates that drug interactions are unknown.

8. The system of claim 1, wherein the anesthetic agent is at least one of Isoflurane, Sevoflurane, Enflurane, and Halothane, and wherein the threshold value is at least one of the following:
   when the fraction of inspired anesthetic agent is greater than about 0.3%,
   when the effect site concentration of the anesthetic agent is greater than about 0.3%, or when the end tidal anesthetic agent is greater than about 0.3%.

9. The system of claim 1, wherein the anesthetic agent is Desflurane and the threshold value is at least one of the following:
   when the fraction of Desflurane is greater than about 0.3%,
   when the effect site concentration of Desflurane is greater than about 0.3% times a minimum aveolar concentration accounting for patient age ($MAC_{age}$), or when the end tidal Desflurane is greater than about 0.3%.

10. The system of claim 1, wherein the anesthetic agent is $N_2O$ and the threshold value is at least one of the following:
    when the fraction of $N_2O$ is greater than about 0.3%,
    when the effect site concentration of $N_2O$ is greater than about 0.3% times the minimum effect site concentration of the $N_2O$, or
    when the end tidal $N_2O$ is greater than about 0.3%.

11. The system of claim 1, wherein the anesthetic agent is a least one of Isoflurane, Sevoflurane, Enflurane, and Halothane and the threshold value is when the effect site concentration of the anesthetic agent is greater than about 0.3% * a minimum alveolar concentration accounting for patient consciousness (Age MAC awake).

12. The system of claim 1, wherein the anesthetic agent is $N.sub.2O$ and the threshold value is when the effect site concentration of $N_2O$ is greater than about 0.1*Age MAC awake.

13. A system for displaying a PK/PD drug model for a patient, the system comprising:
    a treatment device, wherein the treatment device provides an anesthetic agent to the patient;
    a display, wherein real-time PK/PD data associated the anesthetic agent provided to the patient is displayed on the display; and
    a safety controller, wherein the safety controller detects a predetermined fraction of anesthetic agent that exceeds a predetermined threshold value and further sends a signal to the display to terminates display of real-time PK/PD data for the anesthetic agent, and further wherein the safety controller determines whether an interaction threshold is met, and removes any interaction effects.

14. The system of claim of 13, wherein the system terminates display of real-time PK/PD data when the effect site concentration for the anesthetic agent remains below a predetermined level for a predetermined time period.

15. The system of claim 13, wherein the system terminates display of real-time PK/PD data when one or more monitored anesthetic agents have a positive fraction inspired value or a positive end tidal value and wherein all anesthetic agents remain below the threshold value for a predetermined time period.

16. The system of claim 13, wherein the system terminates display of real-time PK/PD data when a monitored respiration rate and heart rate are invalid or when the monitor is disconnected.

17. The system of claim 13, wherein the system displays an end case message when the threshold value is detected.

18. A computerized method for displaying a PK/PD drug model for a patient, the method comprising the steps of:
   detecting a quantity of the anesthetic agent provided to the patient with a monitor; and
   displaying with a safety controller on a display real-time PK/PD data associated with the anesthetic agent, wherein the safety controller detects a predetermined fraction of anesthetic agent that exceeds a predetermined threshold value and further sends a signal to the display, and further wherein the safety controller determines whether an interaction threshold is met, and removes any interaction effects.

* * * * *